United States Patent
Ganion

(10) Patent No.: US 7,239,927 B2
(45) Date of Patent: Jul. 3, 2007

(54) IMPLANTABLE MEDICAL DEVICE INCLUDING SELF-BOOTSTRAPPED THERAPY PULSE OUTPUT CIRCUIT SWITCHES

(75) Inventor: Vincent P. Ganion, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 283 days.

(21) Appl. No.: 11/097,668

(22) Filed: Mar. 31, 2005

(65) Prior Publication Data

US 2006/0224200 A1   Oct. 5, 2006

(51) Int. Cl.
*A61N 1/00* (2006.01)

(52) U.S. Cl. .................................... 607/148; 128/897
(58) Field of Classification Search ............ 607/148
See application file for complete search history.

(56) References Cited

U.S. PATENT DOCUMENTS 6,643,546 B2 * 11/2003 Mathis et al. ............. 607/9

* cited by examiner

*Primary Examiner*—Carl Layno
*Assistant Examiner*—Yun Haeng Lee
(74) *Attorney, Agent, or Firm*—Daniel G. Chapik; Girma Wolde-Michael

(57) ABSTRACT

An implantable medical device (IMD) includes one or more semiconductor switches and one or more switch driver circuits. The semiconductor switches, in response to one or more switch-on and switch-off commands that each have a voltage magnitude, switch between a conductive state and a non-conductive state, respectively, to thereby selectively supply one or more therapy pulses using electrical energy from an electrical energy source. The switch driver circuits, in response to drive commands, selectively supply the switch-on and switch-off commands to the semiconductor switches. The switch driver circuits, using a portion of the supplied therapy pulses, increase the voltage magnitudes of the switch-on and switch-off commands to a magnitude that maintains the switch in the conductive state or the non-conductive state, respectively, while the therapy pulses are being supplied.

18 Claims, 8 Drawing Sheets

IMPLANTABLE MEDICAL DEVICE INCLUDING SELF-BOOTSTRAPPED THERAPY PULSE OUTPUT CIRCUIT SWITCHES

FIELD OF THE INVENTION

The present invention relates to implantable medical devices (IMDs) and, more particularly, to an IMD that includes a therapy pulse output circuit having self-bootstrapped switches.

BACKGROUND OF THE INVENTION

Various types of devices have been developed for implantation into the human body to provide various types of health-related therapies, diagnostics, and/or monitoring. Examples of such devices, generally known as implantable medical devices (IMDs), include various types of cardiac rhythm management devices, such as cardiac pacemakers, cardioverter/defibrillators, cardiomyostimulators. Some IMDs may also be configured as various physiological stimulators including, for example, nerve, muscle, and deep brain stimulators, or as various types of physiological monitors, or drug delivery systems, just to name a few. Some IMDs include varying amounts of electronic memory that may be used to store not only device operating and control software, but to store various types of patient- and device-related data. In addition, some of these same IMDs may include signal processing and telemetry circuitry, which allows some or all of the data stored in the memory to be transmitted to a remote computer network or other communication node, and/or the device to receive and store data transmitted to it remotely from a computer network or other communication node.

The above-mentioned devices are typically implanted in a convenient location usually under the skin of the user and in the vicinity of the one or more major arteries or veins. One or more electrical leads connected to the pacemaker are inserted into or on the heart of the user, usually through a convenient vein or artery. The ends of the leads typically include one or more electrodes that are placed in contact with the walls or surface of one or more chambers of the heart, depending upon the particular therapies deemed appropriate for the user. The IMD may include a plurality of semiconductor switches, such as MOS transistors, that are selectively transitioned between conductive and non-conductive states to supply one or more cardiac pacing pulses to one or more of the electrodes, to stimulate the heart in one of several ways, again depending upon the particular therapy being delivered. The leads may also be configured to simultaneously sense the physiologic signals provided by the heart to determine when to deliver a therapeutic pulse to the heart, and the nature of the pulse, e.g., a pacing pulse or a defibrillation shock.

The type and number of electrodes associated with a lead may vary depending, for example, on the particular cardiac therapies being delivered. For example, the leads in many IMDs include at least a tip electrode and a ring electrode, and the leads in some IMDs additionally include a coil electrode. In this latter instance, the MOS pacing switches in the IMD may be configured to supply a pacing pulse either between the tip electrode and the ring electrode or between the ring electrode and the coil electrode. In such instances, it is possible that the control voltages supplied to the MOS transistor gates may need to be larger in magnitude than the highest magnitude IMD system supply voltages in order to maintain the MOS transistor in its conductive state or its non-conductive state.

More specifically, if the pacing switches are implemented using NMOS transistors, the control voltage may need to be a value that is more positive than the positive-most IMD system supply voltage in order to maintain the NMOS transistor in its conductive state, and the control voltage may need to be a value that is more negative than the negative-most IMD system supply voltage in order to maintain the NMOS transistor in its non-conductive state. Alternatively, if the pacing switches are implemented using PMOS transistors, the control voltage may need to be a value that is more negative than the negative-most IMD system supply voltage in order to maintain the PMOS transistor in its conductive state, and the control voltage may need to be a value that is more positive than the positive-most IMD system supply voltage in order to maintain the PMOS transistor in its non-conductive state.

The above-described MOS transistor gate voltages could be realized by including additional components within the IMD control circuitry, and/or by including additional regulated power supplies within the system. However, this could lead to undesirable increases in device implementation costs.

Hence, there is a need for a system and method of supplying MOS semiconductor pacing switch gate voltages that have sufficient magnitudes to keep the switches in a commanded conductive state without having to provide additional components within the IMD control circuitry and/or additional regulated power supplies within the system. The present invention addresses at least this need.

BRIEF SUMMARY OF THE INVENTION

In one embodiment, and by way of example only, an implantable medical device (IMD) includes one or more semiconductor switches and one or more switch driver circuits. The one or more semiconductor switches are adapted to receive electrical energy from an electrical energy source, and are each coupled to receive one or more switch-on and switch-off commands. The switch-on and switch-off commands each have a voltage magnitude, and each semiconductor switch is operable, upon receipt of the switch-on and switch-off commands, to switch between a conductive state and a non-conductive state, respectively, to thereby selectively supply one or more therapy pulses using the electrical energy from the electrical energy source. The one or more switch driver circuits are adapted to receive drive commands and are operable, in response thereto, to selectively supply the switch-on and switch-off commands to at least one of the semiconductor switches. Each switch driver circuit is coupled to receive a portion of the supplied therapy pulses and is configured to increase the voltage magnitudes of the switch-on and switch-off commands to a magnitude that maintains the switch in the conductive state or the non-conductive state, respectively, while the therapy pulses are being supplied.

In another exemplary embodiment, an implantable medical device for delivering one or more therapy pulses to a patient includes a therapy energy supply circuit, a control circuit, one or more semiconductor switches, and one or more switch driver circuits. The therapy energy supply circuit is configured to store and supply electrical energy. The control circuit is configured to supply drive commands. The one or more semiconductor switches are adapted to receive electrical energy from an electrical energy source, and are each coupled to receive one or more switch-on and switch-off commands. The switch-on and switch-off commands each have a voltage magnitude, and each semiconductor switch is operable, upon receipt of the switch-on and switch-off commands, to switch between a conductive state and a non-conductive state, respectively, to thereby selectively supply one or more therapy pulses using the electrical energy from the electrical energy source. The one or more switch driver circuits are adapted to receive the drive commands and are operable, in response thereto, to selectively supply the switch-on and switch-off commands to at least one of the semiconductor switches. Each switch driver circuit is coupled to receive a portion of the supplied therapy pulses and is configured to increase the voltage magnitudes of the switch-on and switch-off commands to a magnitude that maintains the switch in the conductive state or the non-conductive state, respectively, while the therapy pulses are being supplied.

In yet another exemplary embodiment, in an implantable medical device (IMD) having a plurality of semiconductor switches that are to configured transition between a conductive state and a non-conductive state to thereby selectively deliver a therapy pulse having electrical energy, a method of maintaining the semiconductor switches in the conductive state or the non-conductive state during delivery of the therapy pulses includes the steps of supplying switch-on and switch-off commands to the semiconductor switches to thereby cause the semiconductor switches to transition to the conductive state and the non-conductive state, respectively. The switch-on and switch-off commands each have a voltage magnitude. A portion of the electrical energy of the delivered therapy pulse is used to increase the voltage magnitude of the switch-on and switch-off commands to magnitudes that maintain the semiconductor switches in the conductive state and the non-conductive state, respectively.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description of the drawings. In this regard, before proceeding with the detailed description, it is to be appreciated that the described embodiment is not limited to use in conjunction with a specific type of implantable medical device (IMD). Thus, although the present embodiment is, for convenience of explanation, depicted and described as being implemented in an implantable cardioverter-defibrillator (ICD), it will be appreciated that it can be implemented in various other IMDs.

Figure 1:
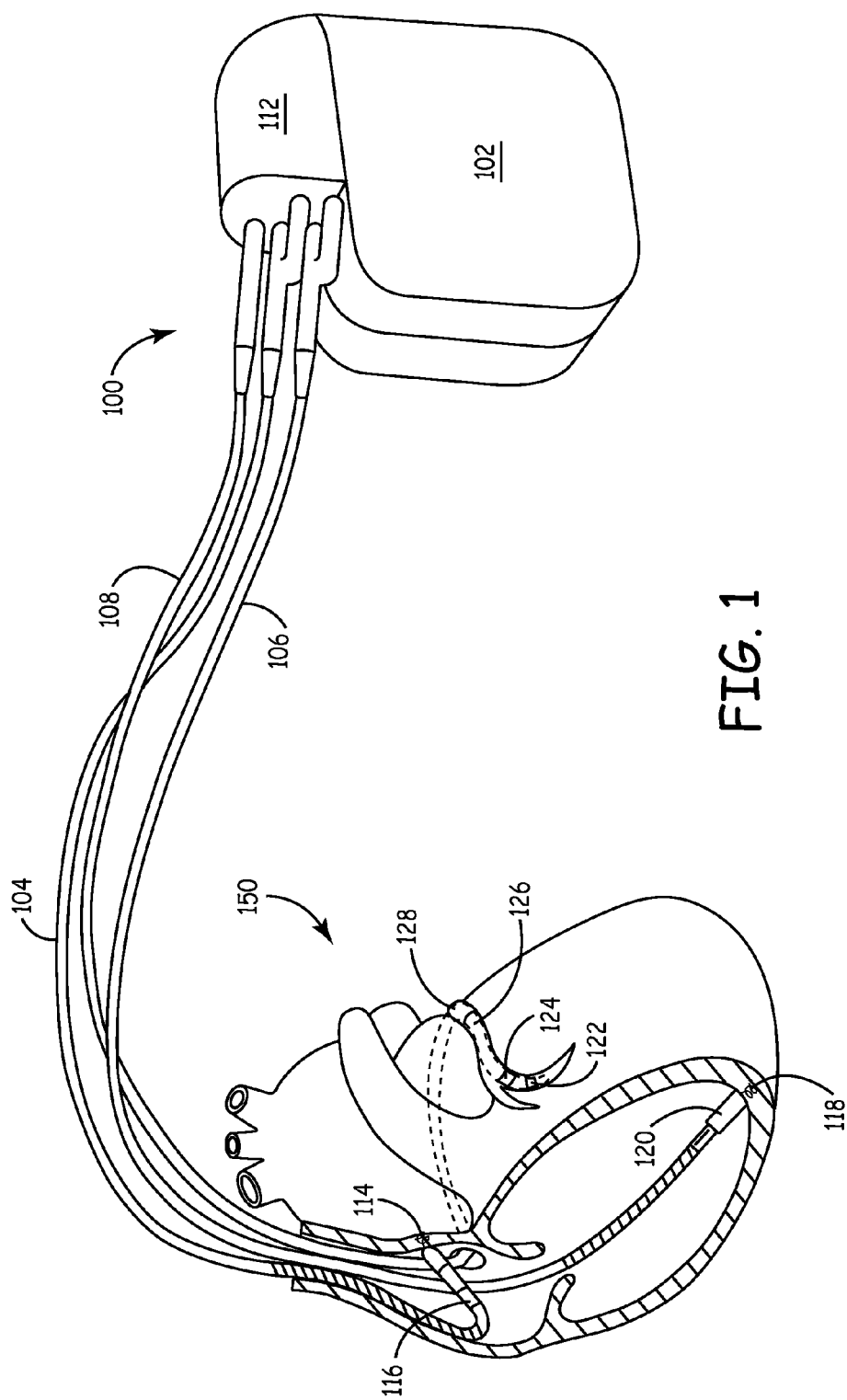
FIG. 1 is a perspective view of an implantable cardio-defibrillator coupled to a heart and which is exemplary of one type of implantable medical device (IMD) that may incorporate an embodiment of the present invention.

Turning now to the description and with reference first to FIG. 1, a simplified representation of an ICD 100 and its connection to a patient heart 150 is shown. The ICD 100 includes a housing 102 and a plurality of leads, including a first lead 104, a second lead 106, and a third lead 108. The housing 102 is preferably formed of a suitable, internal body compatible material that has been approved for medical use, such as, for example, titanium. The housing 102 is preferably hermetically sealed, so that it is substantially impervious to body fluids, and is suitably physiologically shaped to substantially avoid any sharp edges, so that tissue damage during and after implantation can be substantially avoided. The housing 102 includes a connector header 112, which includes separate connector ports and feedthroughs (neither are shown), at least one for each lead 104-108. The connector ports each electrically couple one of the leads 104-108 to one of the feedthroughs, which in turn electrically couples the connector port to the associated circuitry housed within the housing 102. A detailed description of at least a portion of this circuitry is provided further below.

The first, second, and third leads 104-108, each of which include a plurality of electrodes, extend subcutaneously from the housing 102 and include a plurality of electrodes that can be used for pacing, sensing, and/or cardioversion/defibrillation. When implanted in a patient, the first lead 104 extends into the right atrial chamber of the heart 150, where it is coupled to the right atrial wall. In the depicted embodiment, the first lead 104 is implemented as a bipolar endocardial lead and includes an atrial tip (ATIP) pace/sense electrode 114 and an atrial ring (ARING) pace/sense electrode 116. During cardiac pacing operations, cardiac pacing pulses are delivered, and atrial depolarization events are sensed, between the atrial tip and atrial ring pace/sense electrodes 114 and 116. It will be appreciated that in an alternative embodiment, the first lead 104 could be implemented as a unipolar endocardial lead. In such an alternative embodiment, the housing 102 would function as one of the atrial pace/sense electrodes.

The second lead 106 extends through the right atrial chamber of the heart 150 and into the right ventricle, where it is coupled to the right ventricle wall. In the depicted embodiment, the second lead 106 is implemented as a bipolar endocardial lead and includes a right ventricle tip (RVTIP) pace/sense electrode 118 and a right ventricle ring (RVRING) pace/sense electrode 120. During cardiac pacing operations, cardiac pacing pulses are delivered, and right ventricular depolarization events are sensed, between the right ventricular tip and right ventricular ring pace/sense electrodes 118 and 120. As with the first lead 104, it will be appreciated that the second lead 106 could alternatively be implemented as a unipolar endocardial lead, rather than as a bipolar lead.

The third lead 108, similar to the second lead 106, passes through the right atrial chamber of the heart 150. However, rather than extending into the right ventricle, the third lead 108 extends through the coronary sinus, and into the great vein 128 proximate the left ventricle of the heart 150. In the depicted embodiment, the third lead 108 is also implemented as a bipolar endocardial lead, and thus includes a left ventricle tip (LVTIP) pace/sense electrode 122, a left ventricle ring (LVRING) pace/sense electrode 124, and a right ventricle coil (LVCOIL) electrode 126. During cardiac pacing operations, cardiac pacing pulses are delivered, and left ventricular depolarization events are sensed, between the left ventricular tip and left ventricular ring pace/sense electrodes 122 and 124. In the depicted embodiment, left ventricular pace pulses and/or ventricular depolarization events may also be delivered and/or sensed between the left ventricular ring pace/sense electrode 124 and the right ventricular coil electrode 126. As with the first and second leads 104 and 106, it will be appreciated that the third lead 108 could alternatively be implemented as a unipolar endocardial lead, rather than as a bipolar lead.

In describing the depicted ICD 100 above, each of the "pace/sense" electrodes were described as preferably implementing both pacing and sensing functions. It will nonetheless be appreciated that the pace/sense electrodes may be implemented exclusively as pace or sense electrodes, or may be implemented in programmed combinations for sensing cardiac signals and delivering cardiac pacing pulses along programmed pacing and sensing vectors. It will additionally be appreciated that the ICD 100 may be used to deliver cardioversion-defibrillation shocks may be applied, when needed, between selected pairs of the electrodes 114-126, according to any one of numerous defibrillation regimens.

Figure 2:
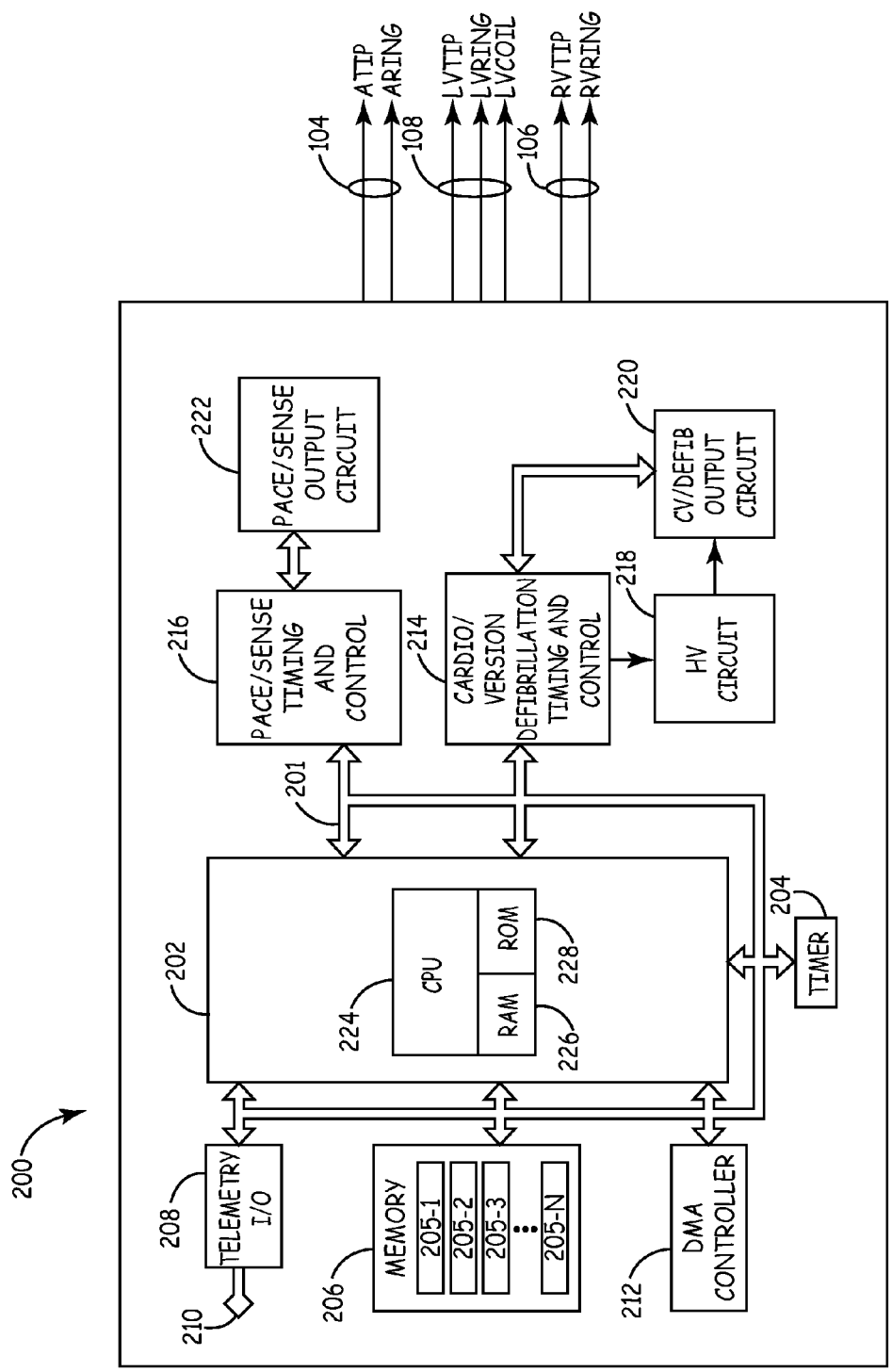
FIG. 2 is a functional block diagram of an exemplary circuit architecture that may be included in the IMD of FIG. 1.

As was noted above, the ICD 100 includes circuitry within the housing 102 that is used to control the overall operation of the ICD 100. At least a portion of this circuitry is illustrated in FIG. 2, and will now be described in more detail. The circuitry 200 illustrated in FIG. 2 includes a controller circuit 202 and various other functional circuit blocks 204-218 that are in operable communication with, and which may be operated under control of, the controller circuit 202 via, for example, a common communications data bus 201. It will be appreciated that the circuitry depicted in FIG. 2 is merely exemplary of a particular architecture, and that numerous other circuit architectures may be used to implement the operation of the ICD 100. The controller circuit 202 includes, among other things, a CPU (central processing unit) 224, which may include on-board RAM (random access memory) 226, and on-board ROM (read only memory) 228. The CPU 224 may be any one of numerous known general purpose processors or an application specific processor that operates in response to program instructions. Such program instructions may be stored in either or both the RAM 226 and the ROM 228. For example, the operating system software may be stored in the ROM 228, whereas various operating mode software routines and various operational parameters may be store in the RAM 226. It will be appreciated that this is merely exemplary of one scheme for storing operating software and software routines, and that various other storage schemes may be implemented. It will also be appreciated that the controller circuit 202 may be implemented using various other circuits, not just a programmable processor. For example, digital logic circuits and analog signal processing circuits could also be used.

A clock/timer circuit 204 provides one or more clock and timing signals to the controller circuit 202 and, if needed, to various ones of the other functional blocks 206-218. The clock and timing signals provide for the proper synchronous operation of the various functional circuits that make up the circuitry 200. The clock/timer circuit 204 may be any one of numerous known circuits for providing clock and/or timing signals. Non-limiting examples include various types of crystal oscillators, such as a temperature compensated crystal oscillator (TXCO), a micro-computer compensated crystal oscillator (MCXO), and an oven controlled crystal oscillator (OCXO).

A memory circuit 206 is in operable communication with the controller circuit 202 via the communications data bus 201. The memory circuit 206 includes a plurality of memory registers 205-1, 205-2, 205-2, . . . 205-N, in which various types of data are stored. The data that the memory circuit 206 stores in its memory registers 205 may include both device-related data and physiological-related data. It will be appreciated that one or more memory circuits 206 may be in operable communication with the controller circuit 202 to store such data. It will also be appreciated that the memory circuit 206 could be integrally formed as part of the controller circuit 202 and/or CPU 224, RAM 226, and/or ROM 228, or could be part of a device or system that is physically separate from the ICD 100. The data that may be stored in memory circuit 206 include, but are not limited to, various types of patient-related data, and various types of device-related data.

Some or all of the data stored in the memory circuit 206 may be read and transmitted to an external transceiver (not shown). Moreover, data may be received from an external transceiver and written into the memory circuit 206. To implement this functionality, the ICD circuitry 200 includes a telemetry input/output (I/O) circuit 208 and an antenna 210. The telemetry I/O circuit 208 is coupled to the antenna 210 and, as its name connotes, functions as an input device, or receiver, when the antenna 210 is receiving data transmitted to the ICD 100, and functions as an output device, or transmitter, when data are being transmitted from the ICD 100. The data transmitted to and from the ICD 100 is done so using radio frequency (RF) waves. Thus, the telemetry I/O circuit 208 includes one or more RF signal sources that may be used to demodulate the data received by the ICD 100, and to modulate the data being transmitted by the ICD 100. The telemetry I/O circuit 208 may also function to decode interrogation signals it receives from an external transceiver and transfer these decoded signals to the controller circuit 202. The controller circuit 202 may then appropriately command the telemetry I/O circuit 208 to be configured to transmit or receive data.

In the depicted embodiment, a DMA (direct memory access) controller 212 is in operable communication with the controller circuit 202. The DMA controller 212, as is generally known, provides direct memory access to memory circuit memory registers 205, or to the RAM 226 or ROM 228, without involving the CPU 224. This can conserve battery power and simplify data read and write operations. It will be appreciated that the DMA controller 212 could be omitted or could form an integral part of the controller circuit 220.

A cardioversion/defibrillation timing and control circuit 214 and a pace/sense timing and control circuit 216 are each coupled to the controller circuit 202 via the communications data bus 201. The cardioversion/defibrillation timing and control circuit 214, in response to instructions from the controller circuit 202, controls the operations of a high voltage (HV) circuit 218 and a cardioversion/defibrillation output circuit 220 to deliver cardioversion/defibrillation shock therapy pulses when needed such as, for example, in the event an atrial or ventricular fibrillation or flutter, or a malignant high rate tachycardia, is detected. The high voltage circuit 218 stores and supplies relatively high voltage energy using, for example, a non-illustrated charging circuit to charge one or more non-illustrated high voltage capacitors to a relatively high voltage. The cardioversion/defibrillation output circuit 220 includes a plurality of high voltage switches (not shown) that deliver the shock therapy pulses to selected ones of the depicted electrodes 114-126 and/or other non-illustrated electrodes. The cardioversion/defibrillation output circuit 220, in response to the cardioversion/defibrillation timing and control circuit 214, determines whether a monophasic or biphasic therapy pulses are delivered.

The pace/sense timing and control circuit 216 is programmable and, in response to instructions from the controller circuit 202, controls a pacing output circuit 222 to deliver cardiac pacing pulses to the heart 150 in accordance with any one of numerous atrial and ventricular pacing operational modes. The pace/sense timing and control circuit 216, together with the pacing output circuit 222, may also implement various tachyarrhythmia detection and classification operations. The pacing output circuit 222, like the cardioversion/defibrillation output circuit 220, includes a plurality of switches, which are not shown in FIG. 2, that deliver the shock therapy pulses to selected ones of the depicted electrodes 114-126. The pacing output circuit 222 additionally includes a pacing energy supply circuit, which is also not shown in FIG. 2. The pacing energy supply circuit stores and supplies the electrical energy that is delivered to the selected electrodes 114-126 as cardiac pacing pulses. A more detailed depiction of a particular embodiment of a portion of the pacing output circuit, illustrating how cardiac pacing pulses may be supplied to the left ventricular pace/sense electrodes 120-126, is shown in FIG. 3 and with reference thereto will now be described in more detail.

Figure 3:
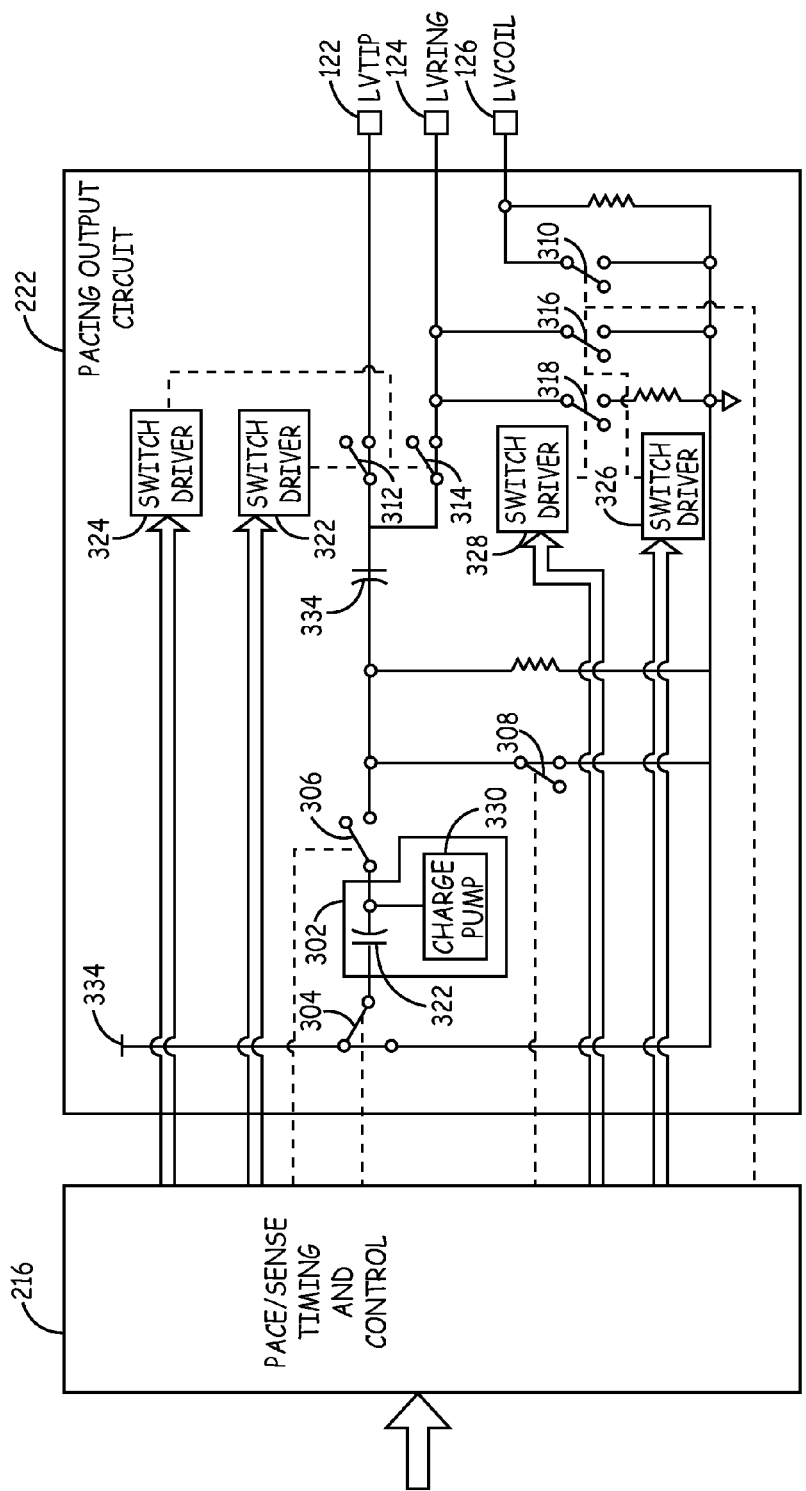
FIG. 3 is a simplified schematic diagram of a pacing output circuit according to an exemplary embodiment of the present invention that may be used to implement the circuit architecture of FIG. 2.

As FIG. 3 shows, the pacing output circuit 222 includes the above-mentioned pacing energy supply circuit 302, a plurality of controllable switches 304-318, and a plurality of switch driver circuits 322-328. The pacing energy supply circuit 302 includes a charge pump 330 and a pacing pulse charge capacitor 332. The charge pump 330, when instructed to do so by the pace/timing and control circuit 216, charges the pacing pulse charge capacitor 332 to a predetermined voltage magnitude, which may depend, for example, on the particular pacing mode being implemented. In any case, it will be appreciated that in order for the charge pump 330 to charge the pacing pulse charge capacitor 332, controllable switches 304 and 306 are preferably positioned as shown in FIG. 3, which electrically couples the pacing pulse charge capacitor 332 in series between the charge pump 330 and circuit node 334, and electrically decouples the pacing pulse charge capacitor 332 from the remaining portions of the pacing output circuit 222.

The controllable switches 304-318 are each dual-position switches and are each responsive to switch commands to move to one of the two positions. Preferably, each controllable switch 304-318 is implemented as a semiconductor switch, and even more preferably using one or more MOS transistors, which may be NMOS, PMOS, or both. For example, in a particular preferred embodiment, switch 304 is implemented using two PMOS transistors, though it will be appreciated that it could also be implemented as an MOS inverter. The remaining switches 306-318 are preferably implemented as either NMOS or PMOS transistors that are configured, in response to received switch commands, to switch to between a conductive state and a non-conductive state. It will be appreciated, however, that one or more of these remaining switches 306-318 could be implemented in any one of numerous other configurations.

No matter how the controllable switches 304-318 are implemented, in the depicted embodiment the switch commands supplied to each switch 304-318 are supplied from one or more associated switch driver circuits. In the depicted embodiment, the switch driver circuits associated with controllable switches 304-310 are not separately shown, but are instead depicted as being implemented as part of the pace/sense timing and control circuit 216. Conversely, the switch driver circuits 322-328 associated with controllable switches 312-318, respectively, are shown separate from the pace/sense timing and control circuit 216. It will be appreciated that this is done merely for illustrative and descriptive convenience, and that the non-illustrated switch driver circuits could be implemented separate from the pace/sense timing and control circuit 216. Moreover, the switch driver circuits 322-328, while shown separate from the pace/sense timing and control circuit 216, could be implemented as part of the pace/sense timing and control circuit 216.

In any case, the switch driver circuits associated with each of the switches 304-318 are each coupled to receive drive commands from the pace/sense timing and control circuit 216 and are configured, in response to the received drive commands, to supply appropriate switch commands to its associated switch. In the depicted embodiment, switch driver circuits 322-328, in response to the received drive commands, supply switch-on and switch-off commands to the MOS switches 312-318, respectively, which cause the MOS switches 312-318 to switch between the conductive and non-conductive state, respectively. Since the controllable switches 304-318 are preferably implemented as semiconductor switches, and most preferably as MOS transistors, it will be appreciated that the switch commands are supplied to the associated gate of each controllable switch 304-318. The switch commands each have an appropriate voltage magnitude that will cause the controllable switch 304-318 to either conduct (e.g., "close/on") or not conduct (e.g., "open/off"). The pacing switch drivers 322-328 also receive operational command signals from the pace/sense timing and control circuit 216. The purpose for this will be described in more detail further below.

In the depicted embodiment, the pace/sense timing and control circuit 216 and the pacing output circuit 222 are configured such that, at least for the left ventricle, pacing pulses can be supplied between the tip pace/sense electrode 122 (LVTIP) and the ring pace/sense electrode 124 (LVRING), or between the ring pace/sense electrode 124 (LVRING) and the coil electrode 126 (LVCOIL). When the tip pace/sense electrode 122 (LVTIP) is the pacing drive node, initially switches 304, 306, 312, 316, and 318 are closed and switches 308, 310, and 314 are open. In this configuration, a pacing pulse is supplied from the pacing pulse charge capacitor 332, through switch 306, a coupling capacitor 334, switch 312, from the tip pace/sense electrode 122 (LVTIP) to the ring pace/sense electrode 124 (LVRING), and then through switches 316 and 304. When the ring pace/sense electrode 124 (LVRING) is the pacing drive node, initially switches 304, 306, 310, and 314 are closed and switches 308, 312, 316, and 318 are open. In this configuration, a pacing pulse is supplied from the pacing pulse charge capacitor 332, through switch 306, coupling capacitor 334, and switch 314, from the ring pace/sense electrode 124 (LVRING) to the coil electrode 126 (LV-COIL), and then through switches 310 and 304.

In both of the above-described instances, it will be appreciated that some of the delineated switches, as well as switch 308 may be selectively opened and closed to implement fast discharge and slow discharge functions as part of the pacing pulse cycle. A detailed description of each of these functions is not necessary to understand the instant invention, and will therefore not be provided. Before proceeding further, it is noted that hereinafter switches 312-318 are referred to as pacing switches, as these are the switches that control which of the electrodes 118, 120, 122 are used to supply cardiac pacing pulses.

As was previously noted, with the depicted configuration certain pacing events can occur that may result in the need to increase the voltage magnitude of one or more of the switch commands supplied to the pacing switches 312-318 to a value that exceeds the maximum power supply voltage magnitudes. Thus, the driver circuits 322-328 associated with pacing switches 312-318 are configured to provide this functionality. More specifically, the switch driver circuits 322-328 use energy from the supplied cardiac pacing pulses to self-bootstrap the pacing switches 312-318 in the desired state. A particular preferred embodiment of a switch driver circuit 400 that may be used to implement the switch driver circuits 322-328 is shown in FIG. 4, and will now be described in more detail.

The switch driver circuit 400 includes a switch signal supply circuit 402, a capacitance circuit element 404, and a logic circuit 406. The switch signal supply circuit 402 includes an input node 401 that is coupled to receive the drive commands from the pace/sense timing and control circuit 216 and is operable, in response to the drive commands, to supply the switch-on and switch-off commands via an output node 403. To implement this functionality, the switch signal supply circuit 402 includes a first inverter circuit 408, a second inverter circuit 410, an upper gate drive circuit 412, and a lower gate drive circuit 414. Particular embodiments of each of these circuits will now be described in more detail, beginning with the first inverter circuit 408.

The first inverter circuit 408 is implemented, at least in the depicted embodiment, as an MOS inverter, that includes an input terminal 416 and an output terminal 418. The input terminal 416 is coupled to the switch signal supply circuit input node 401 and thus receives the drive commands supplied from the pace/sense timing and control circuit 216. The first inverter circuit 408, upon receipt of the drive commands, supplies circuit control signals to its output terminal 418. The second inverter circuit 410 is substantially identical to the first inverter circuit 408 and as such also includes an input terminal 420 and an output terminal 422. The second inverter circuit input terminal 420 is coupled to the first inverter circuit output terminal 418 and thus receives the circuit control signals. The second inverter circuit 410, upon receipt of the circuit control signals, supplies a signal representative of either the switch-on command or the switch-off command to its output terminal 422.

Figure 4:
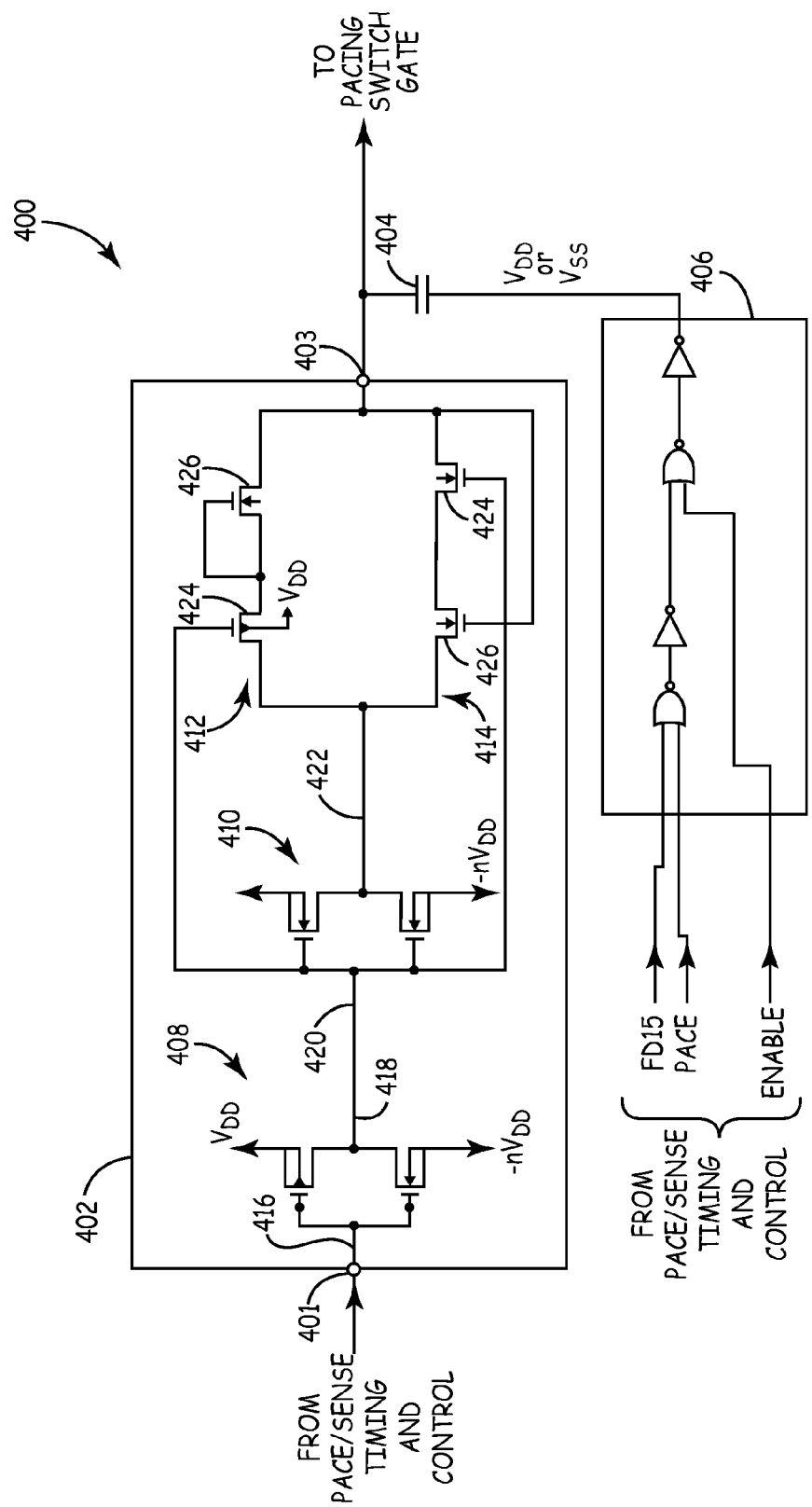
FIG. 4 is a schematic diagram of a switch driver circuit according to an exemplary embodiment of the present invention that may be included in the pacing output circuit of FIG. 3.

As FIG. 4 also shows, the first and second inverter circuits 408 and 410, in addition to including input and output terminals 416, 420 and 418, 422, respectively, are also each coupled to two voltage sources. One of the voltage sources ($V_{DD}$) is a relatively positive polarity voltage source, and the other source ($-nV_{DD}$) is a relatively negative polarity voltage source that has a relatively large magnitude (e.g., $n \times V_{DD}$). Thus, in the depicted embodiment, the circuit control signals supplied by the first inverter circuit 408 and the signals representative of either the switch-on command or the switch-off command supplied by the second inverter circuit 410 will have voltage values of either $V_{DD}$ or $-nV_{DD}$.

The upper and lower gate drive circuits 412, 414 each include a semiconductor switch 424 and a diode circuit element 426. In both circuits 412, 414, the semiconductor switch 424 and the diode circuit element 426 are electrically coupled in series between the second inverter circuit output terminal 422 and the switch signal supply circuit output node 403. In the depicted embodiment, the semiconductor switches 424 and diode circuit elements 426 in both gate drive circuits 412, 414 are implemented as MOS transistors. More specifically, the semiconductor switch 424 and diode circuit element 426 in the upper gate drive circuit 412 are implemented as a PMOS transistor and an NMOS transistor, respectively, whereas the semiconductor switch 424 and diode circuit element 426 in the lower gate drive circuit 414 are both implemented as NMOS transistors. It will be appreciated that this is merely exemplary, and that various other circuit elements could be used to implement both the upper and lower gate drive circuits 412, 414.

Irrespective of the specific circuit elements that are used, it is seen that the control terminal (e.g., the gate) of the semiconductor switches 424 in the upper and lower gate drive circuits 412, 414 are each electrically coupled to the first inverter circuit output terminal 418. Thus, the semiconductor switches 424 are each responsive to the circuit control signals to selectively switch between a conductive state and a non-conductive state. As will be described more fully below, the diode circuit elements 426 are electrically coupled in the upper and lower gate drive circuits 412, 414 so that current will only flow through its associated circuit 412 or 414 when needed to do so, even if its associated semiconductor switch 424 is in the conductive state.

Turning now to the remainder of the switch driver circuit 400, it is seen that the capacitance circuit element 404 is coupled to the switch signal supply circuit output node 403 and the logic circuit 406. The capacitance circuit element 404 is configured to store a charge, using a portion of the energy from the supplied therapy pulses, that increases the voltage magnitudes of the switch-on and switch-off commands that the switch signal supply circuit 402 supplies. It will be appreciated that the capacitance value of the capacitance circuit element 404 (e.g., $C_{404}$) may vary, but is preferably chosen so that the charge thereon increases the switch-on and switch-off command voltage magnitudes to values that are sufficient to maintain the associated pacing switch 312-318 in the conductive state or the non-conductive state, as appropriate, while the therapy pulses are being supplied.

Figure 5:
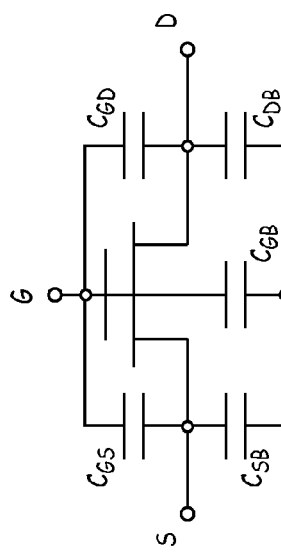
FIG. 5 is a schematic representation of a metal-oxide-semiconductor (MOS) transistor that may be used in the pacing output circuit of FIG. 3 and that depicts the various parasitic capacitances associated with the MOS transistor.

To implement the above-described function, the capacitance circuit element 404 is electrically coupled in series with the parasitic capacitance of its associated pacing switch 312-318, via the logic circuit 406. As is generally known, most semiconductor switches, including MOS transistors, exhibit various parasitic capacitances, such as junction capacitances. For example, as shown in FIG. 5, MOS transistors, such as the ones used to implement the pacing switches 312-318, typically exhibit gate-to-source parasitic capacitance ($C_{gs}$), gate-to-drain parasitic capacitance ($C_{gd}$), source-to-body parasitic capacitance ($C_{sb}$), gate-to-body parasitic capacitance ($C_{gb}$), and drain-to-body parasitic capacitance ($C_{db}$). Returning once again to FIG. 4, it will be appreciated that the particular parasitic capacitance (or capacitances) with which the capacitance circuit element 404 is electrically coupled may vary depending, for example, on whether the associated pacing switch 312-318 is an NMOS transistor or a PMOS transistor. In the depicted implementation, in which the pacing switches 312-318 are implemented as NMOS transistors, the capacitance circuit element 404 is electrically coupled in series with the gate-to-source parasitic capacitance (not shown in FIG. 4) of the associated pacing switch 312-318.

As was noted above, the capacitance circuit element 404 is also electrically coupled to the logic circuit 406. The logic circuit 406 functions to selectively couple the capacitance circuit element 404 to one of two voltage potentials, either a relatively positive voltage potential (e.g., $V_{DD}$) or a relatively negative (or zero) voltage potential (e.g., $V_{SS}$). As was previously mentioned, the logic circuit 406 receives operational command signals from pace/sense timing and control circuit 216. The operational command signals are signals that represent whether the IMD 100 is using the associated pacing switch 312-318 to operate in a particular pacing mode. For example, in the depicted embodiment the operational command signals represent whether the IMD 100 is using the associated pacing switch 312-318 to implement a pacing therapy pulse supply function (PACE) or to implement a fast discharge function (FDIS). If the associated pacing switch 312-318 is not being used to implement either of these functions, the logic circuit 406 couples the relatively negative voltage potential (e.g., $V_{SS}$) to the capacitance circuit element 404. If, however, the associated pacing switch 312-318 is being used to implement either of these functions, the logic circuit 406 couples the relatively positive voltage potential (e.g., $V_{DD}$) to the capacitance circuit element 404. It will be appreciated that the logic circuit 406 may be implemented in any one of numerous configurations, using any one of numerous logic circuits (either discrete or integrated), and that the logic circuit 406 shown in FIG. 4 is merely exemplary of a particular preferred embodiment.

Having described the general configuration and function of the switch driver circuit 400, and each of the individual circuits that comprise the switch driver circuit 400, a more detailed description of how each of the individual circuits function together to implement the described functionality will now be described. In doing so, reference should first be made to FIGS. 6-8, in which like reference numerals refer to like components of those shown in FIG. 4. In providing this description, it is assumed that the tip pace/sense electrode 122 (LVTIP) is the pacing drive node during a large negative pacing pulse delivery. Thus, pacing switches 312, 316, and 318 are being supplied with switch-on commands from the respective associated switch driver circuits 322, 326, and 328, and pacing switch 314 is being supplied with a switch-off command from its associated switch driver circuit 324.

Figure 6:
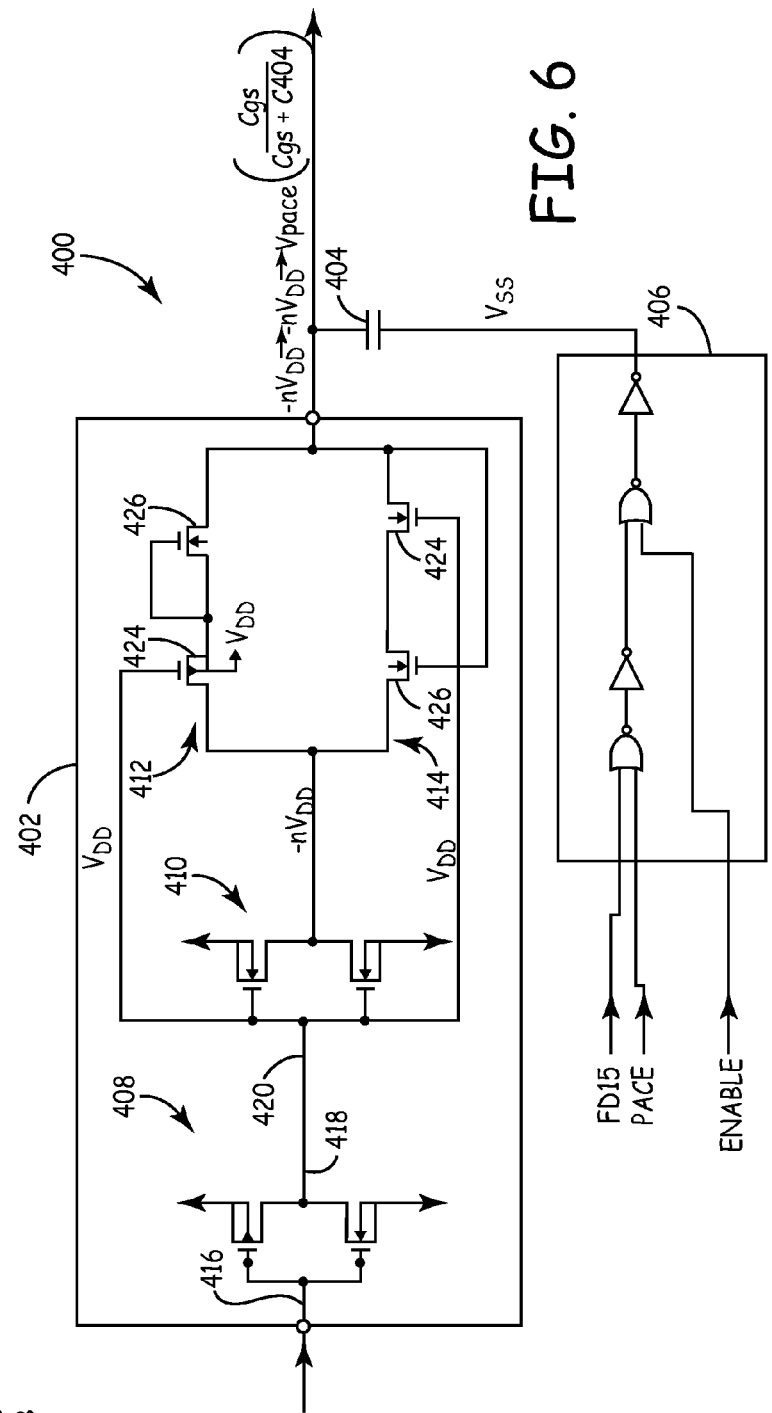
FIG. 6 is a schematic diagram of the switch driver circuit shown in FIG. 4 illustrating various node voltages therein when the circuit is commanding an associated pacing switch to its non-conductive state during delivery of a relatively large pacing pulse.

Starting first with the switch driver circuit 324 for pacing switch 314, the voltage magnitudes at various nodes within the switch driver circuit 324 are as shown in FIG. 6. As shown therein, when the large negative pacing pulse occurs, the negative transition of the pacing pulse voltage will place charge on capacitance circuit element 404 via the capacitance divider formed by capacitance circuit element 404 and the parasitic capacitance of the pacing switch 314. The charge on capacitance circuit element 404 will cause the voltage magnitude of the switch-off command to increase sufficiently (e.g., go sufficiently negative) to keep pacing switch 314 in the "off" or non-conductive state. It may additionally be seen in FIG. 6 that the upper gate driver circuit semiconductor switch 424 is in its non-conductive state, thus no current will flow through the upper gate driver circuit diode circuit element 426. Moreover, although and the lower gate drive circuit semiconductor switch 424 is in its conductive state, the lower gate driver circuit diode circuit element 426 prevents the switch-off command from being pulled back up to $-nV_{DD}$.

Figure 7:
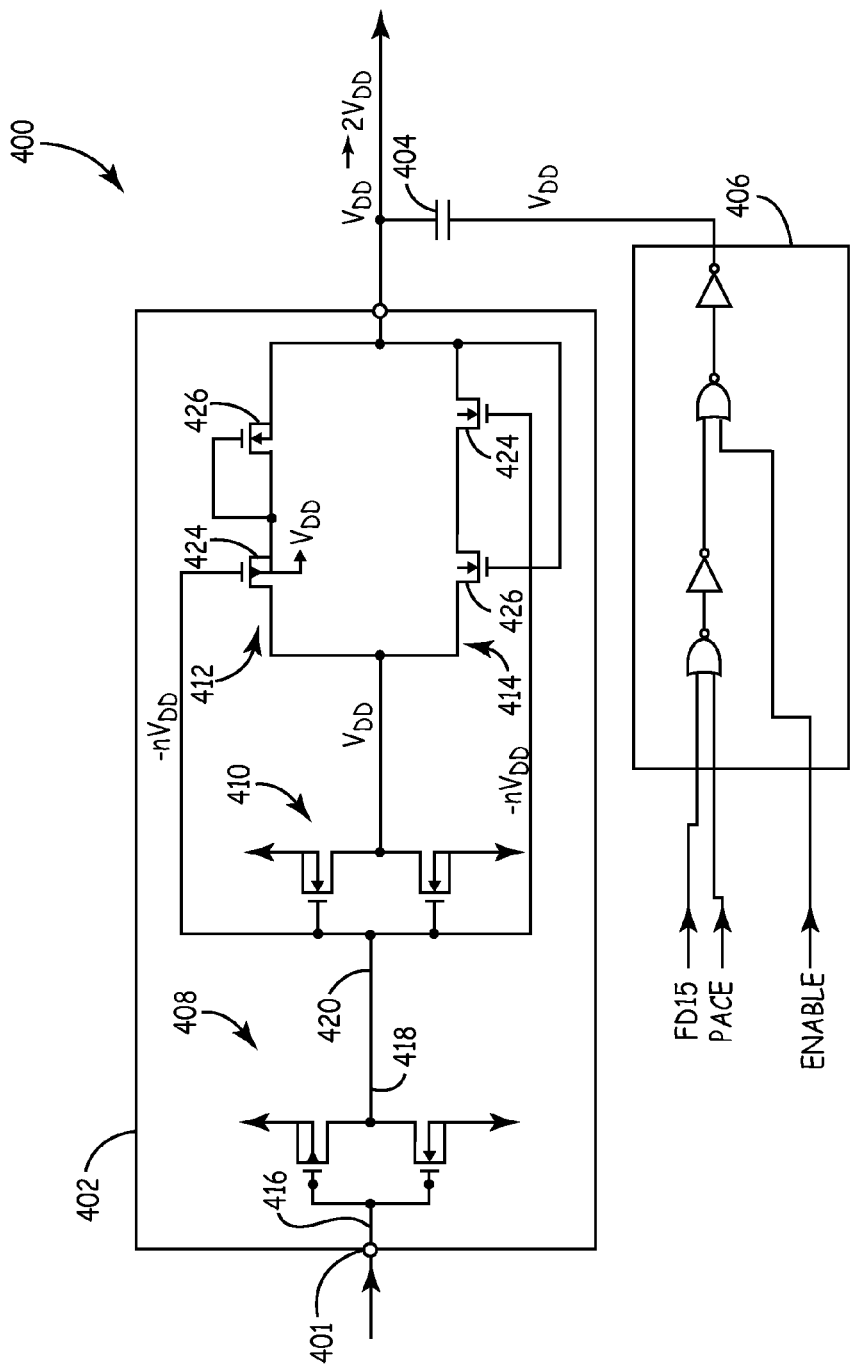
FIG. 7 is a schematic diagram of the switch driver circuit shown in FIG. 4 illustrating various node voltages therein when the circuit is commanding an associated pacing switch to its conductive state during delivery of a relatively large pacing pulse.

Turning now to FIG. 7, the voltage magnitudes at various nodes within the switch driver circuits 322, 326, 328 for pacing switches 312, 316, 318 are shown. As shown therein, when the large negative pacing pulse occurs, the negative transition of the pacing pulse voltage will attempt to place charge on capacitance circuit element 404 via the capacitance divider formed by capacitance circuit element 404 and the parasitic capacitance of the associated pacing switch 312, 316, 318. However, because the upper gate driver circuit semiconductor switch 424 is in its conductive state, the upper gate driver circuit diode circuit element 426 will ensure that the switch-on command voltage magnitude is not reduced by more than a transistor threshold voltage magnitude. Moreover, the lower gate drive circuit semiconductor switch 424 is in its non-conductive state, thus the lower gate driver circuit diode circuit element 426 will not pull the switch-on command down to $V_{DD}$.

Figure 8:
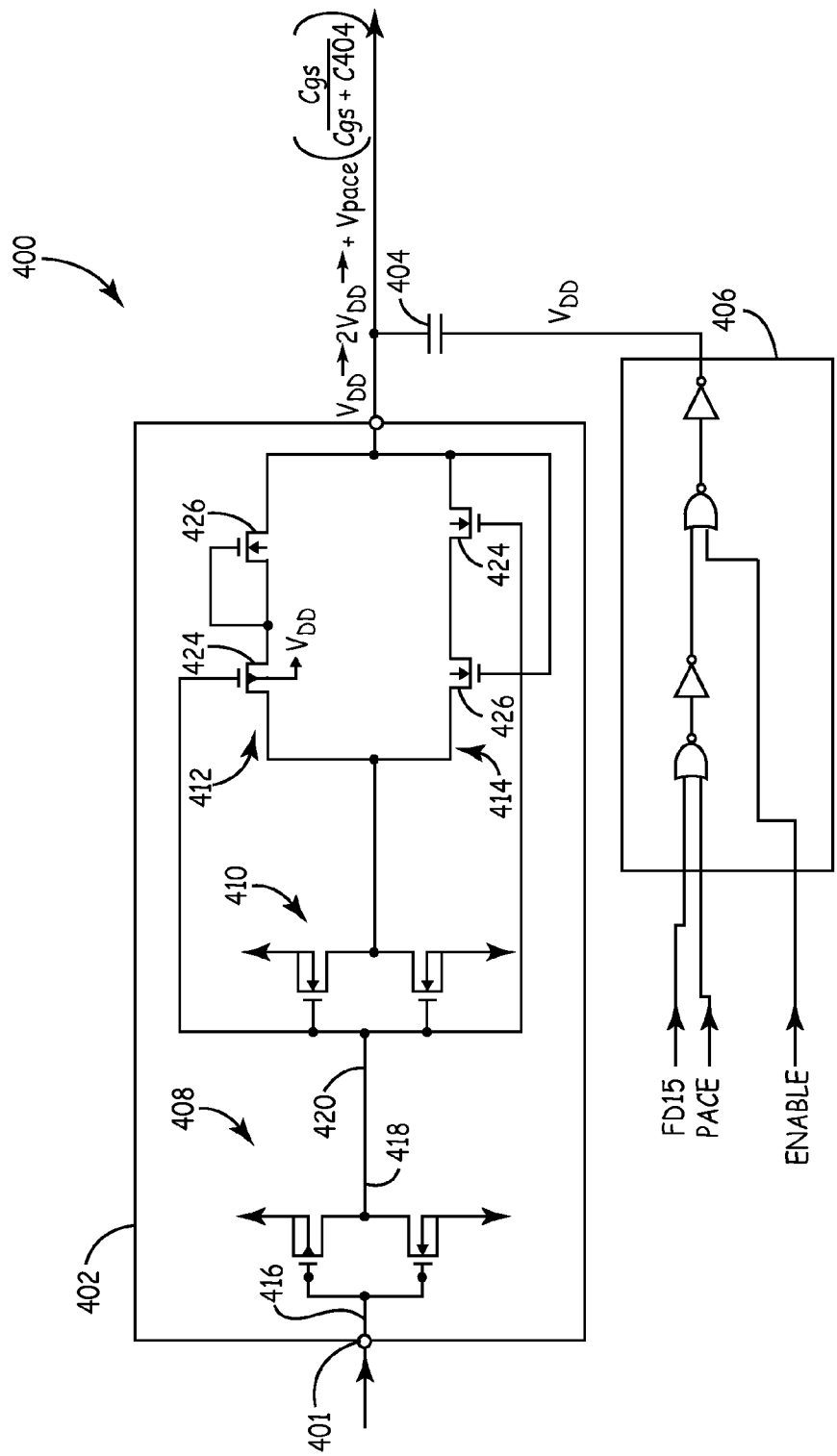
FIG. 8 is a schematic diagram of the switch driver circuit shown in FIG. 4 illustrating various node voltages when the circuit is commanding an associated pacing switch to its conductive state during delivery of a relatively large fast discharge pulse.

As was alluded to above and as is generally known, a cardiac therapy pacing pulse cycle will, in most instances, include either or both a fast discharge function and a slow discharge function following delivery of a pacing pulse. During the fast discharge, the relative voltage magnitude between the pacing switch gate and drain terminals could attain a value that would cause the pacing switch to transition to the non-conductive state. However, as shown in FIG. 8, the positive transition of the fast discharge voltage, along with the positive voltage transition that occurs on the negative plate of the capacitance circuit element 404, places charge on the capacitance circuit element via the capacitance divider formed by capacitance circuit element 404 and the parasitic capacitance of the associated pacing switch 312-318. The charge on capacitance circuit element 404 will cause the voltage magnitude of the switch-on command to increase sufficiently (e.g., go sufficiently positive) to keep the associated pacing switch 314 in the "on" or conductive state. It may additionally be seen in FIG. 8 that the lower gate driver circuit semiconductor switch 424 is in its non-conductive state, thus no current will flow through the lower gate driver circuit diode circuit element 426. Moreover, although and the upper gate drive circuit semiconductor switch 424 is in its conductive state, the upper gate driver circuit diode circuit element 426 prevents the switch-on command from being pulled down to $V_{DD}$.

Figure 9:
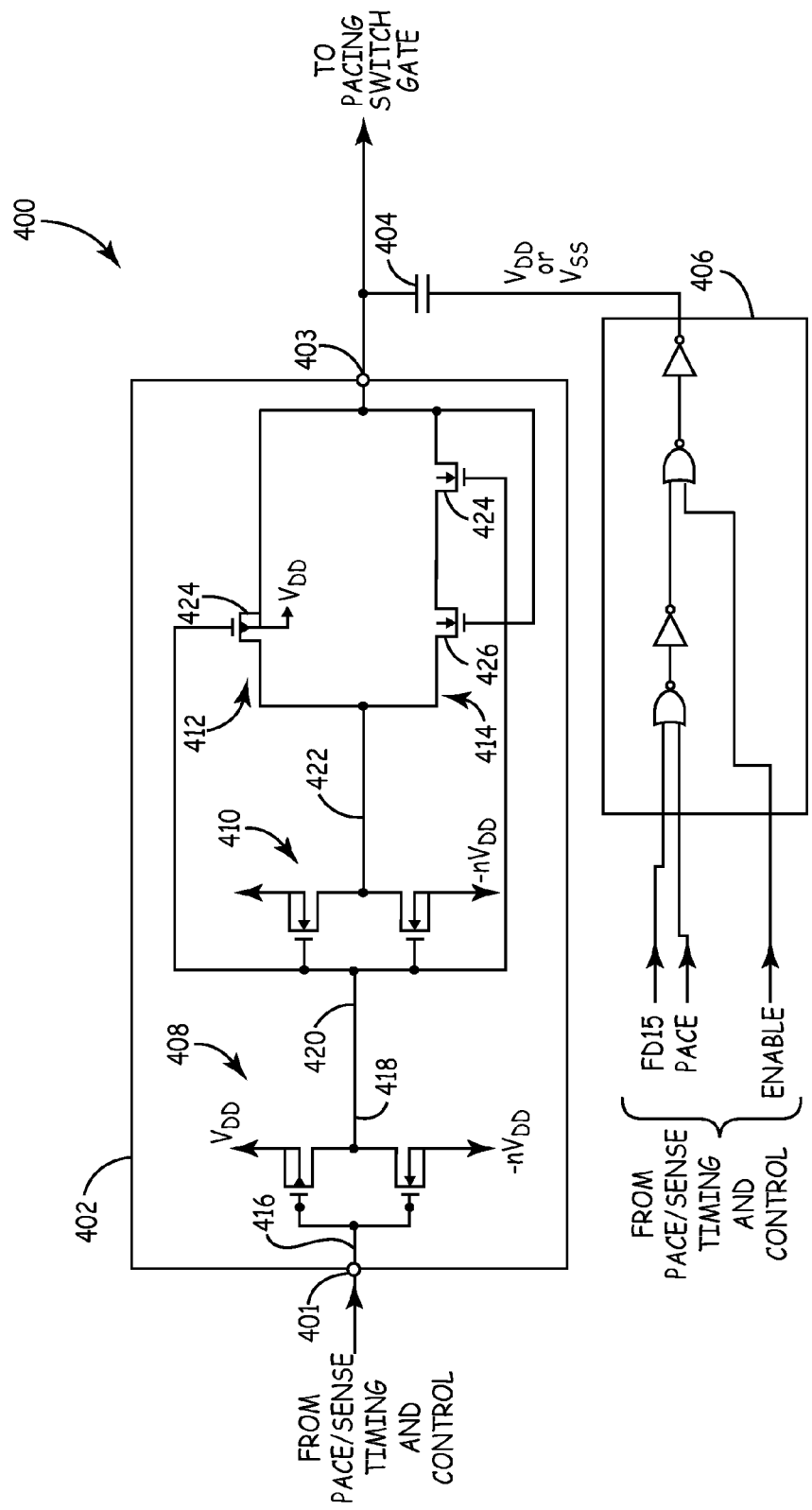
FIG. 9 is a schematic diagram of a switch driver circuit according to an exemplary alternative embodiment of the present invention that may be included in the pacing output circuit of FIG. 3.

In some instances, one or more of the pacing switches 312-318 may be configured within the pacing output circuit 222 such that the voltage magnitude of the switch-on and/or the switch-off commands will remain sufficiently high to keep the switch in the conductive or non-conductive state, as the case may be. For example, and with reference once again to FIG. 3, pacing switch 316 is coupled within the pacing output circuit 222 such that the switch-on command supplied from its switch driver circuit 326 will always be sufficiently high to keep it in its conductive state. Thus, as shown in FIG. 9, the switch driver circuit 326 for this pacing switch 316 may be implemented without the diode circuit element 426 in the upper gate drive circuit 412.

It will be appreciated that the functionality of the switch driver circuits 322-328 described above relies, at least in part, on proper selection of capacitance value of the capacitance circuit element 404 used for each switch driver circuit. Thus, the skilled artisan will appreciate that the capacitance value is chosen so that the charge division between the capacitance circuit element 404 and the associated pacing switch parasitic capacitance during a pace or a fast discharge is such that the associated pacing switch remains on even if the voltage value on the drain (or source) exceeds $V_{DD}$, or remains off even if the voltage value on the drain (or source) goes more negative than $-nV_{DD}$. The skilled artisan will additionally appreciate that capacitance value of the capacitance circuit element 404 is also chosen so that the charge division between the capacitance circuit element 404 and the associated pacing switch parasitic capacitance is such that the drain-to-source voltage magnitudes in the associated switch driver circuit do not exceed a first predetermined magnitude (e.g., ±17 VDC) when the associated pacing switch is in the conductive state, or a second predetermined magnitude (e.g., ±15.5 VDC) when the associated pacing switch is in the non-conductive state. It will be appreciated that the specific values of the capacitance circuit element 404, and of the first and second predetermined voltage magnitudes may vary depending, for example, on the specific circuit design and/or one or more semiconductor process parameters, and that these values may be readily determined by the skilled artisan.

While an exemplary embodiment(s) has been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide those skilled in the art with a convenient road map for implementing a preferred embodiment of the invention. It being understood that various changes may be made in the function and arrangement of elements described in an exemplary preferred embodiment without departing from the spirit and scope of the invention as set forth in the appended claims.

The invention claimed is:

1. An implantable medical device (IMD), comprising:
one or more semiconductor switches adapted to receive electrical energy from an electrical energy source, each semiconductor switch coupled to receive one or more switch-on and switch-off commands, the switch-on and switch-off commands each having a voltage magnitude, each semiconductor switch operable, upon receipt of the switch-on and switch-off commands, to switch between a conductive state and a non-conductive state, respectively, to thereby selectively supply one or more therapy pulses using the electrical energy from the electrical energy source; and
one or more switch driver circuits, each switch driver circuit adapted to receive drive commands and operable, in response thereto, to selectively supply the switch-on and switch-off commands to at least one of the semiconductor switches, each switch driver circuit coupled to receive a portion of the supplied therapy pulses and configured to increase the voltage magnitudes of the switch-on and switch-off commands to a magnitude that maintains the switch in the conductive state or the non-conductive state, respectively, while the therapy pulses are being supplied.

2. The IMD of claim 1, wherein each semiconductor switch includes a parasitic capacitance, and wherein each switch driver circuit comprises:
a capacitance circuit element electrically coupled in series with the semiconductor switch parasitic capacitance, the capacitance circuit element configured to store a charge, using the portion of the supplied therapy pulses, that increases the voltage magnitudes of the switch-on and switch-off commands to the magnitude that maintains the switch in the conductive state or the non-conductive state, respectively, while the therapy pulses are being supplied.

3. The IMD of claim 2, wherein:
each switch driver circuit includes an output node coupled to receive the switch-on and switch-off commands and supply the switch-on and switch-off commands to the at least one semiconductor switches;
the capacitance circuit element includes at least a first terminal and a second terminal, the first terminal coupled to the switch driver circuit output node.

4. The IMD of claim 3, further comprising:
a logic circuit coupled to receive one or more operational commands and operable, in response thereto, to selectively supply the capacitance circuit element second terminal with a voltage signal of either a first magnitude or a second magnitude.

5. The IMD of claim 2, wherein each switch driver circuit further comprises:
a switch signal supply circuit coupled to receive the drive commands and operable, in response thereto, to supply the switch-on and switch-off commands.

6. The IMD of claim 5, wherein each switch signal supply circuit comprises:
an input circuit node and an output circuit node, the input circuit node coupled to receive a signal representative of either the switch-on command or the switch-off command;
a first circuit including a diode and a semiconductor switch electrically coupled in series between the input circuit node and the output circuit node, the first circuit semiconductor switch coupled to receive a circuit control signal and operable, in response thereto, to selectively switch between a conductive state and a non-conductive state, to thereby electrically couple and electrically decouple, respectively, the input circuit node from the output circuit node via the first circuit path; and
a second circuit including a diode and a semiconductor switch electrically coupled in series between the input circuit node and the output circuit node, and electrically coupled in parallel with the first circuit, the second circuit semiconductor switch coupled to receive the circuit control signal and operable, in response thereto, to selectively switch between a conductive state and a non-conductive state, to thereby electrically couple and electrically decouple, respectively, the input circuit node from the output circuit node via the second circuit path.

7. The IMD of claim 6, wherein the diodes in the first and second circuits are each semiconductor switches electrically connected in a diode-configuration.

8. The IMD of claim 6, each switch signal supply circuit further comprises:

an inverter circuit including at least an input terminal and an output terminal, the inverter circuit input terminal coupled to receive the circuit control signal and the output terminal electrically coupled to the input circuit node, the inverter circuit operable, upon receipt of the circuit control signal, to supply the signal representative of either the switch-on command or the switch-off command.

9. The IMD of claim 8, wherein the inverter circuit is a first inverter circuit, and wherein each switch signal supply circuit further comprises:
a second inverter circuit including at least an input terminal and an output terminal, the second inverter circuit input terminal coupled to receive the drive commands and the second inverter circuit output terminal electrically coupled to the first inverter circuit input terminal, the second inverter circuit operable, upon receipt of the drive commands, to supply the circuit control signal.

10. An implantable medical device for delivering one or more therapy pulses to a patient, comprising:
a therapy energy supply circuit configured to store and supply electrical energy;
a control circuit configured to supply drive commands;
one or more semiconductor switches adapted to receive electrical energy from an electrical energy source, each semiconductor switch coupled to receive one or more switch-on and switch-off commands, the switch-on and switch-off commands each having a voltage magnitude, each semiconductor switch operable, upon receipt of the switch-on and switch-off commands, to switch between a conductive state and a non-conductive state, respectively, to thereby selectively supply one or more therapy pulses using the electrical energy from the electrical energy source; and
one or more switch driver circuits coupled to receive the drive commands and operable, in response thereto, to selectively supply the switch-on and switch-off commands to at least one of the semiconductor switches, each switch driver circuit coupled to receive a portion of the supplied therapy pulses and configured to increase the voltage magnitudes of the switch-on and switch-off commands to a magnitude that maintains the switch in the conductive state or the non-conductive state, respectively, while the therapy pulses are being supplied.

11. The IMD of claim 10, wherein each semiconductor switch includes a parasitic capacitance, and wherein each switch driver circuit comprises:
a capacitance circuit element electrically coupled in series with the semiconductor switch parasitic capacitance, the capacitance circuit element configured to store a charge, using the portion of the supplied therapy pulses, that increases the voltage magnitudes of the switch-on and switch-off commands to the magnitude that maintains the switch in the conductive state or the non-conductive state, respectively, while the therapy pulses are being supplied.

12. The IMD of claim 11, wherein:
each switch driver circuit includes an output node coupled to receive the switch-on and switch-off commands and supply the switch-on and switch-off commands to the at least one semiconductor switches;
the capacitance circuit element includes at least a first terminal and a second terminal, the first terminal coupled to the switch driver circuit output node.

13. The IMD of claim 12, further comprising:
a logic circuit coupled to receive one or more operational commands and operable, in response thereto, to selectively supply the capacitance circuit element second terminal with a voltage signal of either a first magnitude or a second magnitude.

14. The IMD of claim 11, wherein each switch driver circuit further comprises:
a switch signal supply circuit coupled to receive the drive commands and operable, in response thereto, to supply the switch-on and switch-off commands.

15. The IMD of claim 14, wherein each switch signal supply circuit comprises:
an input circuit node and an output circuit node, the input circuit node coupled to receive a signal representative of either the switch-on command or the switch-off command;
a first circuit including a diode and a semiconductor switch electrically coupled in series between the input circuit node and the output circuit node, the first circuit semiconductor switch coupled to receive a circuit control signal and operable, in response thereto, to selectively switch between a conductive state and a non-conductive state, to thereby electrically couple and electrically decouple, respectively, the input circuit node from the output circuit node via the first circuit path; and
a second circuit including a diode and a semiconductor switch electrically coupled in series between the input circuit node and the output circuit node, and electrically coupled in parallel with the first circuit, the second circuit semiconductor switch coupled to receive the circuit control signal and operable, in response thereto, to selectively switch between a conductive state and a non-conductive state, to thereby electrically couple and electrically decouple, respectively, the input circuit node from the output circuit node via the second circuit path.

16. The IMD of claim 15, wherein the diodes in the first and second circuits are each semiconductor switches electrically connected in a diode-configuration.

17. The IMD of claim 15, each switch signal supply circuit further comprises:
an inverter circuit including at least an input terminal and an output terminal, the inverter circuit input terminal coupled to receive the circuit control signal and the output terminal electrically coupled to the input circuit node, the inverter circuit operable, upon receipt of the circuit control signal, to supply the signal representative of either the switch-on command or the switch-off command.

18. The IMD of claim 17, wherein the inverter circuit is a first inverter circuit, and wherein each switch signal supply circuit further comprises:
a second inverter circuit including at least an input terminal and an output terminal, the second inverter circuit input terminal coupled to receive the drive commands and the second inverter circuit output terminal electrically coupled to the first inverter circuit input terminal, the second inverter circuit operable, upon receipt of the drive commands, to supply the circuit control signal.

* * * * *